United States Patent
Blair

(10) Patent No.: US 10,294,184 B2
(45) Date of Patent: May 21, 2019

(54) CATALYSTS FOR THE MECHANOCATALYTIC OXIDATIVE DEPOLYMERIZATION OF POLYMER-CONTAINING MATERIALS AND METHODS OF MAKING OXIDIZED REACTION PRODUCTS USING SAME

(71) Applicant: UNIVERSITY OF CENTRAL FLORIDA RESEARCH FOUNDATION INC., Orlando, FL (US)

(72) Inventor: Richard Blair, Oviedo, FL (US)

(73) Assignee: University of Central Florida Research Foundation Inc, Orlando, FL (US)

( * ) Notice: Subject to any disclaimer, the term of this patent is extended or adjusted under 35 U.S.C. 154(b) by 0 days.

(21) Appl. No.: 14/772,897

(22) PCT Filed: Mar. 7, 2014

(86) PCT No.: PCT/US2014/022143
§ 371 (c)(1),
(2) Date: Sep. 4, 2015

(87) PCT Pub. No.: WO2014/138707
PCT Pub. Date: Sep. 12, 2014

(65) Prior Publication Data
US 2016/0009621 A1 Jan. 14, 2016

Related U.S. Application Data

(60) Provisional application No. 61/774,825, filed on Mar. 8, 2013.

(51) Int. Cl.
*C07C 45/61* (2006.01)
*C07C 45/32* (2006.01)
(Continued)

(52) U.S. Cl.
CPC .............. *C07C 45/61* (2013.01); *B01J 23/002* (2013.01); *B01J 23/10* (2013.01); *B01J 23/34* (2013.01);
(Continued)

(58) Field of Classification Search
CPC .......... C07C 45/61; B01J 23/002; B01J 23/34
See application file for complete search history.

(56) References Cited

U.S. PATENT DOCUMENTS 2,057,117 A * 10/1936 Richter ................... C07C 37/54
530/500
2,686,120 A * 8/1954 Borden ................... C07C 45/32
162/14

(Continued)

FOREIGN PATENT DOCUMENTS

WO     WO 2009/061750     *   5/2009   ............... C13K 2/02

OTHER PUBLICATIONS

Hicks. S.M., et al., Mechanocatalysis for biomass-derived chemicals and fuels, 2010, Green Chem. vol. 12, pp. 468-474.*

(Continued)

*Primary Examiner* — Yate' K Cutliff
(74) *Attorney, Agent, or Firm* — William Fitzpatrick

(57) ABSTRACT

The presently disclosed and/or claimed inventive concept(s) relates generally to oxidative oxidized reaction products made from the mechanocatalytic oxidative depolymerization of lignin. More particularly, but without limitation, the mechanocatalytic oxidative depolymerization of lignin is performed in a non-aqueous/non-solvent based and solvent-free process, i.e., via a solid-solid mechanocatalytic oxidative reaction methodology. In one particular embodiment, the process of making such oxidative oxidized reaction products includes, without limitation, the step of mechanocatalytically reacting an oxidation catalyst with lignin or a (Continued)

lignin-containing material. The oxidative reaction products obtained from the process include, for example, at least one of vanillin, and syringealdehyde, vanillic acid, and syringic acid.

4 Claims, 4 Drawing Sheets

(51) Int. Cl.
| | |
|---|---|
| B01J 27/24 | (2006.01) |
| C07C 45/27 | (2006.01) |
| B01J 23/889 | (2006.01) |
| B01J 23/00 | (2006.01) |
| B01J 23/83 | (2006.01) |
| B01J 23/89 | (2006.01) |
| B01J 23/10 | (2006.01) |
| B01J 23/34 | (2006.01) |
| C07C 47/58 | (2006.01) |
| C07C 51/347 | (2006.01) |
| C07C 65/21 | (2006.01) |

(52) U.S. Cl.
CPC ........... *B01J 23/83* (2013.01); *B01J 23/8892* (2013.01); *B01J 23/8926* (2013.01); *B01J 27/24* (2013.01); *C07C 45/27* (2013.01); *C07C 45/32* (2013.01); *C07C 47/58* (2013.01); *C07C 51/347* (2013.01); *C07C 65/21* (2013.01); *B01J 2523/00* (2013.01)

(56) References Cited

U.S. PATENT DOCUMENTS

| | | | | |
|---|---|---|---|---|
| 2,692,291 | A | * | 10/1954 | Bryan .................... C07C 45/32 422/226 |
| 3,920,750 | A | * | 11/1975 | Katzen .................... B01D 3/22 568/432 |
| 4,075,248 | A | * | 2/1978 | Marshall ................. C07C 45/32 568/432 |
| 4,847,422 | A | * | 7/1989 | Klemola ............... C07C 45/783 568/426 |
| 8,062,428 | B2 | | 11/2011 | Blair et al. |
| 2003/0100807 | A1 | | 5/2003 | Shabtai et al. |
| 2003/0115792 | A1 | | 6/2003 | Shabtai et al. |
| 2009/0118494 | A1 | * | 5/2009 | Blair ........................ C07H 1/06 536/127 |

OTHER PUBLICATIONS

Ge,Y., et al., Stud of PET depolymerization catalyzed by metal oxide with different acidity/basicity under microwave irradiation, 2011, Advanced Materials Research, vols. 233-235, pp. 1076-1079.*
Pepper, J.M., et al., Lignin oxidation. Preferential use of cupric oxide, 1967, Canadian Journal of Chemistry, vol. 45, pp. 3009-3012.*
Borges da Silva, E.A., et al., an integrated process to produce vanillin and lignin based polyurethanes form Kraft lignin, vol. 87, pp. 1276-1292.*
Kamimura, A,, et al., K-birnessite MnOs: a new selective oxidant for benzylic and allylic alcohols, 2011, Tetrahedron Letters vol. 52, pp. 538-540.*
Montanari, et al., Metalloporphyrins Catalyzed Oxidations, 1994, Catalysis by Metal Complexes, vol. 17, edited by Ugo, et al., 6 pages.*
Zakzeski, J., et al., The catalytic Valorization of Lignin for the Production of Renewable Chemicals, 2010, Chem. Rev. vol. 110, No. 6, pp. 3552-3599 (Year: 2010).*
Jun, Young-Si, et al., , From melamine-cyanuric acid supramolecular aggregates to carbon nitride hollow spheres, Feb. 26, 2013, Advanced Functional Materials, vol. 23, No. 29, pp. 3661-3667 (Year: 2013).*
Kleine, T., et al., Mechanochemical degradation of lignin and wood by solvent-free grinding in a reactive medium, Nov. 1, 2012, Green Chemistry, vol. 15, No. 1, pp. 160-166, & title page. (Year: 2012).*
Ibrahim et al., "A Concise Review of the Natural Existance, Synthesis, Properties, and Applications of Syringaldehyde," BioResources 7(3) (2012).
Sun, R. C., Tomkinson, J., Ma, P. L., and Liang, S. F. (2000). "Comparative study of hemicelluloses from rice straw by alkali and hydrogen peroxide treatments," Carbohydrate Polymers 42(2), 111-122.
Itoh et al. "Hepatoprotective Effect of Syringic Acid and Vanillic Acid on CCl4-Induced Liver Injury," Biological and Pharmaceutical Bulletin, vol. 33 (2010) No. 6 p. 983-987.

* cited by examiner

CATALYSTS FOR THE MECHANOCATALYTIC OXIDATIVE DEPOLYMERIZATION OF POLYMER-CONTAINING MATERIALS AND METHODS OF MAKING OXIDIZED REACTION PRODUCTS USING SAME

BACKGROUND

1. Field of the Inventive Concept(s)

The presently disclosed and/or claimed inventive concept(s) relates generally to oxidized reaction products made from the mechanocatalytic oxidative depolymerization of lignin. More particularly, but without limitation, the mechanocatalytic oxidative depolymerization of lignin is performed in a non-aqueous and solvent-free process, i.e., via a solid-solid mechanocatalytic oxidative reaction methodology. In one particular embodiment, the process of making such oxidized reaction products includes, without limitation, the step of mechanocatalytically reacting an oxidation catalyst with lignin or a lignin-containing material. The oxidized reaction products obtained from the process include, for example, at least one of vanillin, syringealdehyde, vanillic acid, and syringic acid.

2. Background of the Inventive Concept(s)

The conversion of lignocellulosic biomass represents a potentially rich source of aromatic compounds and complete depolymerization of lignin within the lignocellulosic biomass can produce salable products such as vanillin, syringealdehyde, vanillic acid, syringic acid, and specialty chemicals that use these compounds as precursor molecules. Markets for these biomass-based materials will expand as demand grows for non-petroleum sourced materials, for example. Current production methods for the extraction of vanillin from Kraft liquor, for example, produce 160 kg of caustic waste for every kilogram of vanillin produced. Profitability can be increased and environmental concerns can be lessened by the development of a scalable process that foregoes such traditional caustic processes for the conversion of biomass materials.

Lignin is a complex chemical compound (shown in FIG. 1) commonly derived from wood as a byproduct of the pulp industry and is an integral part of the secondary cell walls of plants and some algae. It is one of the most abundant organic polymers on Earth, exceeded only by cellulose, embodying approximately 30% of non-fossil organic carbon, and constituting from a quarter to a third of the dry mass of wood. As a biopolymer, lignin is unusual because of its heterogeneity and lack of a defined primary structure. Its most commonly noted function is the support through strengthening of wood (xylem cells) in trees. Global production of lignin is around 1.1 million metric tons per year and is used in a wide range of low volume, niche applications where the form of lignin, but not its quality, is important.

Lignin is a cross-linked racemic macromolecule with molecular masses in excess of 10,000. It is relatively hydrophobic and aromatic in nature. The degree of polymerization in nature is difficult to measure since it is fragmented during extraction, and the molecule consists of various types of substructures that appear to repeat in a haphazard manner (as shown in FIG. 1). There are three monolignol monomers that are methoxylated to various degrees: p-coumaryl alcohol, coniferyl alcohol, and sinapyl alcohol. These lignols are incorporated into lignin in the form of the phenylpropanoids p-hydroxyphenyl (H), guaiacyl (G), and syringyl (S), respectively. Gymnosperms have a lignin content that consists almost entirely of G with small quantities of H, the lignin content of dicotyledonous angiosperms is mostly a mixture of G and S (with very little H), and monocotyledonous lignin is a mixture of all three. Many grasses have mostly G type lignin structures, while some palms have mainly S type lignin structures. The type and amount of lignin depolymerization products (e.g., oxidized reaction products) are dependent on the type and/or amount of a particular type of lignin in the biomass (i.e., H, G, and/or S). That is, the available percentage of precursors in the lignin structure strictly determines the formation of phenolic compounds such as vanillin or syringealdehyde. Lignin is especially useful in producing phenolic aldehydes as it requires fewer transformations or chemical treatments. For example, Sun et al., (2000) found that a yield of about 50 to 59.7% syringaldehyde and vanillin in equal proportions of the total phenolic aldehydes was obtained via nitrobenzene oxidation from lignin extracted from rice straw.

Biodegradation of lignin is a prerequisite for processing biofuel from plant raw materials. Lignin is indigestible by animal enzymes, but some fungi and bacteria are able to secrete ligninases (also named lignases) that are able to inefficiently and non-economically biodegrade the lignin polymer. As such, the presence of lignin within cellulosic or hemicellulosic structures is associated with reduced digestibility of the overall plant biomass.

Vanillin is a phenolic aldehyde having the molecular formula $C_8H_8O_3$ (shown in FIG. 2). Its functional groups include aldehyde, ether, and phenol. It is the primary component of the extract of the vanilla bean. Synthetic vanillin, instead of natural vanilla extract, is sometimes used as a flavoring agent in foods, beverages, and pharmaceuticals. Natural "vanilla extract" is a mixture of several hundred different compounds in addition to vanillin. Artificial vanilla flavoring, on the other hand, is a solution of pure vanillin, usually of synthetic origin.

Due to the scarcity and expense of natural vanilla extract, there has long been interest in the synthetic preparation of its predominant component vanillin. The first commercial synthesis of vanillin began with the more readily available natural compound eugenol. Typically, artificial vanillin is made either from guaiacol or from lignin. Lignin-based artificial vanilla flavoring is alleged to have a richer flavor profile than oil-based flavoring; the difference is most likely due to the presence of acetovanillone in the lignin-derived product, an impurity not found in vanillin synthesized from guaiacol. Synthetic vanillin became significantly more available in the 1930s, when production began using the lignin-containing waste produced by the sulfite pulping process for preparing wood pulp for the paper industry. While some vanillin is still made from lignin wastes, most synthetic vanillin is today synthesized in a two-step process from the petrochemical precursors guaiacol and glyoxylic acid.

Several routes exist for synthesizing vanillin from guaiacol. At present, the most significant of these is a two-step process practiced by Rhodia since the 1970s, in which guaiacol reacts with glyoxylic acid by electrophilic aromatic substitution. The resulting vanillylmandelic acid is then converted via 4-Hydroxy-3-methoxyphenylglyoxylic acid to vanillin by oxidative decarboxylation.

The largest use of vanillin is as a flavoring, usually in sweet foods. The ice cream and chocolate industries together comprise 75% of the market for vanillin as a flavoring, with smaller amounts being used in confections and baked goods. Vanillin is also used in the fragrance industry, in perfumes, and to mask unpleasant odors or tastes in medicines, livestock fodder, and cleaning products. Vanillin has also been used as a chemical intermediate in the production of pharmaceuticals and other fine chemicals. In 1970, more than half the world's vanillin production was used in the synthesis of other chemicals, but as of 2004 such a use only accounted for 13% of the market for vanillin. Additionally, vanillin can be used as a general purpose stain for developing thin layer chromatography (TLC) plates to aid in visualizing components of a reaction mixture.

Vanillic acid (4-hydroxy-3-methoxybenzoic acid) is an odorless dihydroxybenzoic acid derivative and having the formula $C_8H_8O_4$ that is used as a flavoring agent. It is an oxidized form of vanillin. It is also an intermediate in the production of vanillin from ferulic acid. The highest amount of vanillic acid in plants known is found in the root of *Angelica sinensis*, an herb indigenous to China, which is used in traditional Chinese medicine. Açaí oil, obtained from the fruit of the açaí palm (*Euterpe oleracea*), is rich in vanillic acid (1,616±94 mg/kg), for example. It is also one of the main natural phenols in argan oil and is also commonly found in wine and vinegar. Vanillic acid is one of the main catechins metabolites found in humans after consumption of green tea infusions.

Syringealdehyde (also, "syringaldehyde" or 3,5-dimethoxy-4-hydroxybenzaldehyde) is an organic compound having the formula $C_9H_{10}O_4$ (shown in FIG. 3) that occurs in trace amounts throughout nature. Because it may contain many different functional groups, it can be classified in many ways—aromatic, aldehyde, or phenol. It is a colorless solid (impure samples appear yellowish) that is soluble in alcohol and polar organic solvents. Its refractive index is 1.53. Syringealdehyde is very similar in structure to vanillin and has comparable applications. Though not as well-commercialized as vanillin, syringealdehyde chemistry and its manipulation are emerging rather rapidly.

Syringealdehyde is formed in oak barrels and blends into whiskey, giving it a spicy, smoky, hot, and smoldering wood aroma. It is also used in the manufacture of antibacterial drugs including Trimethoprim, Bactrim, and Biseptol where syringealdehyde is an essential intermediate in their production. Bactrim or Biseptol are combinations of Trimethoprim with sulfamethoxazole. Applications for the use of syringealdehyde are diverse: as an antifungal agent for yeast infections and as an antimicrobial for *clostridium*; as an antimicrobial additive to antiseptic paper (thereby reducing the transmission of staph, pneumonia, and *pseudomonas* bacteria); and, it has potent antioxidant properties. See, e.g., Ibrahim et al., "A Concise Review of the Natural Existance, Synthesis, Properties, and Applications of Syringaldehyde," BioResources 7(3) (2012), the entire contents of which is hereby incorporated by reference in its entirety. For example, antioxidant activity for syringealdehyde has been recorded to be six times higher than that of protocatechuic aldehyde and the antioxidant activity of syringealdehyde has been found to be significantly greater than that of vanillin. (Boundagidou et al., 2010).

Lignin, as it is a waste of the pulping industry and a major by-product from the biomass-to-ethanol conversion process, offers a continuous, renewable, and economical supply of syringealdehyde. Syringyl (S) units found in lignin are the source from which syringealdehyde can be obtained when lignin-containing materials undergo certain oxidation reactions.

Syringic acid (4-hydroxy-3,5-dimethoxybenzoic acid) is a naturally occurring O-methylated trihydroxybenzoic acid having a formula of $C_9H_{10}O_5$. It is an oxidized form of syringealdehyde. Syringic acid (as well as vanillic acid) possesses antimicrobial, anti-cancer, and anti-DNA oxidation properties. Additionally, both compounds act as immunomodulators and provide protective effects in mice with liver injuries. See, e.g., Itoh et al. "Hepatoprotective Effect of Syringic Acid and Vanillic Acid on CCl4-Induced Liver Injury," Biological and Pharmaceutical Bulletin, Vol. 33 (2010) No. 6 P 983-987, the entire contents of which is expressly incorporated by reference herein.

Mechanocatalysis or tribocatalysis is a solid-solid reaction using mechanical force without the addition of solvents, i.e., it is a non-aqueous or solvent-free catalytic reaction. Effective mechanocatalysts are mechanically robust and possess sites that are physically accessible and chemically active. Mechanocatalytic processes also typically do not require external heat. Substantially all of the energy for the reaction comes from the pressures and frictional heating provided by the kinetic energy of milling media moving in a container. In a mechanocatalytic system, it is important that intimate contact between the catalyst and reactant is maintained. Pebble (or rolling) mills, shaker mills, attrition mills, and planetary mills are a few examples of mills that effectively "push" the catalyst into contact with the material to be treated in a mechanocatalytic process. A mechanocatalytic process for converting biomass to soluble sugars is, for example, disclosed in U.S. Ser. No. 11/935,712, the entire contents of which are hereby incorporated by reference in their entirety.

One of the ways to convert lignin to fuels or chemicals is by base catalyzed depolymerization followed by hydrotreating, as shown in U.S. Patent publications 2003/0100807A1 and 2003/0115792A1. This process uses a strong base to partially break up the lignin compounds. One problem of this approach is the high consumption of strong base (such as NaOH) which makes the process less economical and environmentally appropriate. One recent study showed, for example, that pH within this process must be above 12.4 in order to achieve a relatively high lignin conversion.

Processes that avoid such a need for strong bases can shift the recovery of organic precursors from biomass to economically viable processes, as well as lessen the cost of environmental protection for such bio-conversion processes.

As such, disclosed and/or claimed herein are processes and methods for economically, safely, and reliably producing oxidized reaction products made from the mechanocatalytic oxidative depolymerization of lignin. More particularly, but without limitation, the mechanocatalytic oxidative depolymerization of lignin is performed in a non-aqueous/solvent-free based process, i.e., via a solid-solid mechanocatalytic oxidative reaction methodology. In one particular embodiment, the process of making such oxidized reaction products includes, without limitation, the step of mechanocatalytically reacting an oxidation catalyst with lignin or a lignin-containing material. The oxidized reaction products obtained from the process include, for example, at least one of vanillin, syringealdehyde, vanillic acid, and syringic acid.

SUMMARY OF THE INVENTIVE CONCEPTS

The presently disclosed and/or claimed inventive concept(s) encompasses an oxidized depolymerization reaction product produced by a non-aqueous and solvent-free catalytic reaction of an amount of a polymer containing material, a lignin containing material for example, but not by way of limitation, and an oxidation catalyst. In an alternate embodiment, the presently disclosed and/or claimed inventive concept(s) encompasses a method for the production of an oxidized reaction product by catalytically reacting an amount of a polymer containing material, a lignin containing material for example, but not by way of limitation, and an oxidation catalyst in a non-aqueous and solvent-free environment for a period of time sufficient to produce the oxidized reaction product.

It is contemplated that the polymer containing material can be a lignin-containing material such as a biomass or lignocellulosic material. In any of the embodiments disclosed and/or claimed herein, the oxidized reaction product may comprise at least one of vanillin, syringealdehyde, vanillic acid, and syringic acid. Additionally, for all embodiments the oxidation catalyst may be, without limitation, a catalytically effective amount of a solid metal oxide. Such catalytically effective amounts of a solid metal oxide may be, for example, but without limitation, at least one of manganese oxides, cerium oxides, and combinations thereof. In one non-limiting embodiment, the oxidation catalyst comprises K-Birnessite when a manganese oxide material is chosen as the oxidation catalyst. Alternatively, the oxidation catalyst may be a porphyrin-like material capable of oxidizing at least a portion of the lignin-containing material. In such embodiments where the oxidation catalyst is a porphyrin-like material, the oxidation catalyst may be for example, but not by way of limitation, a catalytically effective amount of hexagonal carbon nitride.

The presently disclosed and/or claimed inventive concept(s) also encompass a catalytically oxidized reaction product produced by a non-aqueous and solvent-free mechanocatalytic reaction of a lignin-containing material and an oxidation catalyst.

BRIEF DESCRIPTION OF THE SEVERAL VIEWS OF THE DRAWINGS

The inventors have unexpectedly found that when an oxidation catalyst is combined with a lignin-containing material and agitated in a non-aqueous and solvent-free environment, a high yield of oxidized reaction products, including vanillin, syringealdehyde, vanillic acid, and syringic acid can be produced. In the process, the agitation of the lignin-containing material and the oxidation catalyst, typically in a mill, provides the kinetic energy necessary to drive the mechanocatalytic oxidation reaction.

DETAILED DESCRIPTION OF THE INVENTIVE CONCEPT(S)

Figure 1:
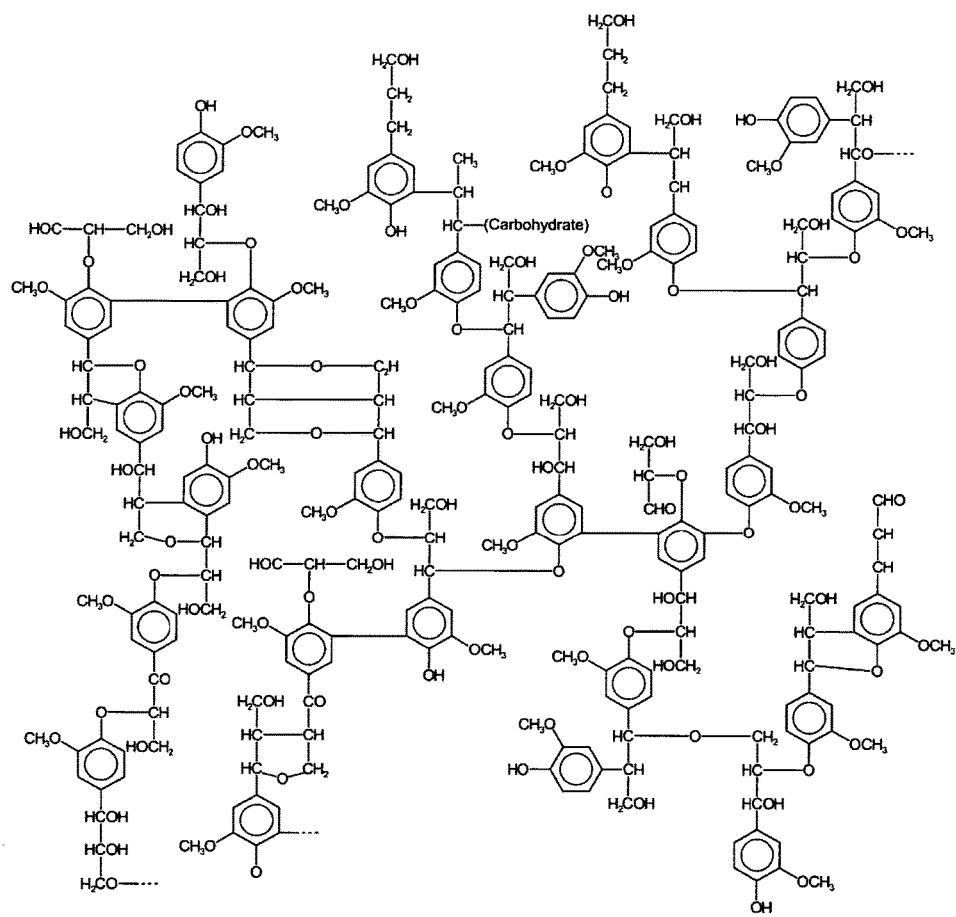
FIG. 1 is a structural representation of the sub-units comprising lignin.
Figure 2:
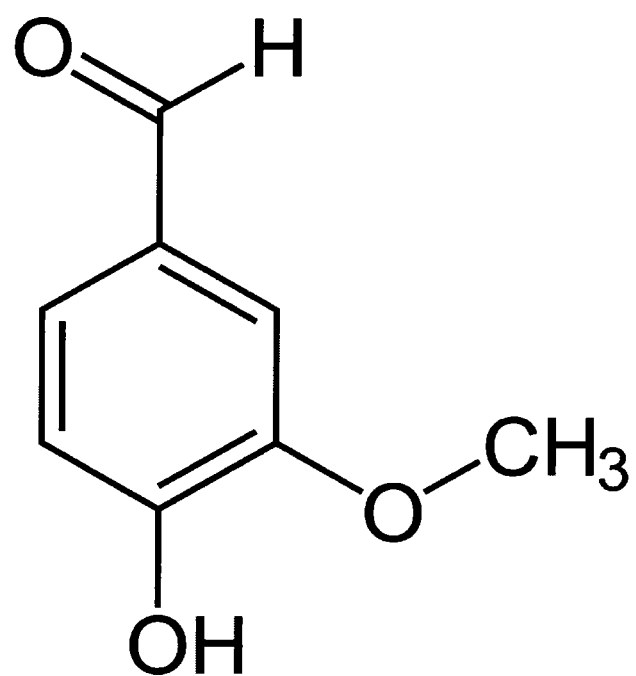
FIG. 2 is a structural representation of vanillin.
Figure 3:
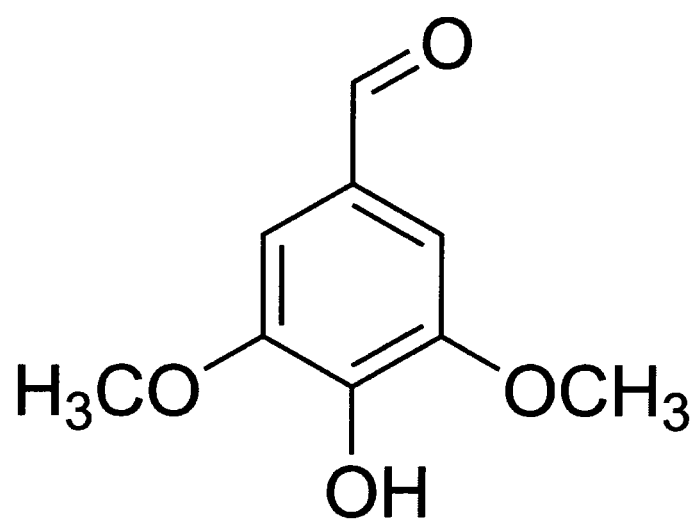
FIG. 3 is a structural representation of syringealdehyde.

Before explaining at least one embodiment of the presently disclosed and/or claimed inventive concept(s) in detail, it is to be understood that the presently disclosed and/or claimed inventive concept(s) is not limited in its application to the details of construction and the arrangement of the components or steps or methodologies set forth in the following description or illustrated in the drawings. The presently disclosed and/or claimed inventive concept(s) is capable of other embodiments or of being practiced or carried out in various ways. Also, it is to be understood that the phraseology and terminology employed herein is for the purpose of description and should not be regarded as limiting.

Unless otherwise defined herein, technical terms used in connection with the presently disclosed and/or claimed inventive concept(s) shall have the meanings that are commonly understood by those of ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which this presently disclosed and/or claimed inventive concept(s) pertains. All patents, published patent applications, and non-patent publications referenced in any portion of this application are herein expressly incorporated by reference in their entirety to the same extent as if each individual patent or publication was specifically and individually indicated to be incorporated by reference.

All of the articles and/or methods disclosed herein can be made and executed without undue experimentation in light of the present disclosure. While the articles and methods of the presently disclosed and/or claimed inventive concept(s) have been described in terms of preferred embodiments, it will be apparent to those of skill in the art that variations may be applied to the articles and/or methods and in the steps or in the sequence of steps of the method described herein without departing from the concept, spirit and scope of the presently disclosed and/or claimed inventive concept(s). All such similar substitutes and modifications apparent to those skilled in the art are deemed to be within the spirit, scope and concept of the presently disclosed and/or claimed inventive concept(s).

As utilized in accordance with the present disclosure, the following terms, unless otherwise indicated, shall be understood to have the following meanings.

The use of the word "a" or "an" when used in conjunction with the term "comprising" in may mean "one," but it is also consistent with the meaning of "one or more," "at least one," and "one or more than one." The use of the term "or" is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects. For example but not by way of limitation, when the term "about" is utilized, the designated value may vary by plus or minus twelve percent, or eleven percent, or ten percent, or nine percent, or eight percent, or seven percent, or six percent, or five percent, or four percent, or three percent, or two percent, or one percent. The use of the term "at least one" will be understood to include one as well as any quantity more than one including, but not limited to, 2, 3, 4, 5, 10, 15, 20, 30, 40, 50, 100, etc. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z. The use of ordinal number terminology (i.e., "first", "second", "third", "fourth", etc.) is solely for the purpose of differentiating between two or more items and is not meant to imply any sequence or order or importance to one item over another or any order of addition, for example.

As used herein, the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC and, if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Figure 4:
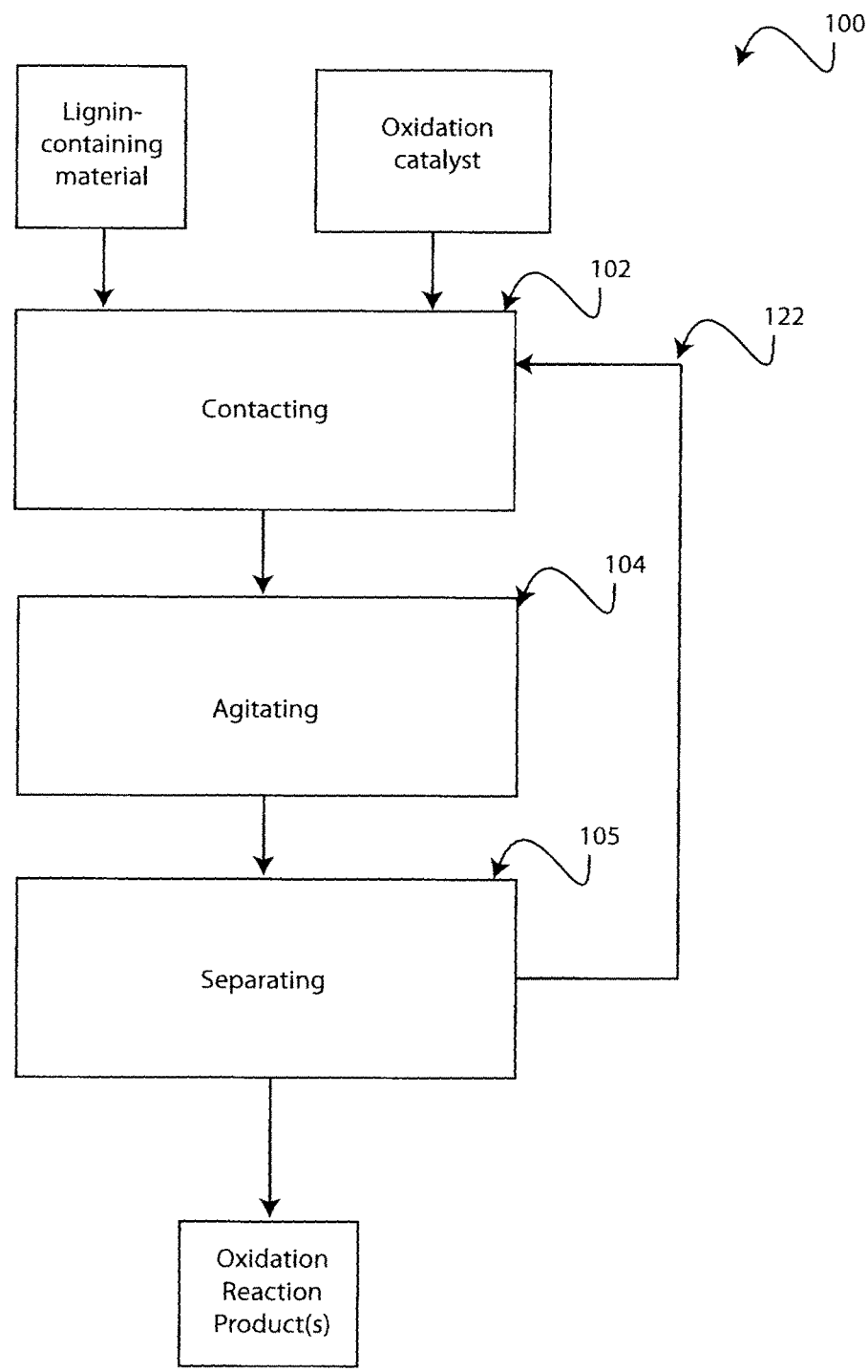
FIG. 4 is a schematic representation of a catalytic process for the production of oxidized depolymerization reaction products from a lignin-containing material and an oxidation catalyst.

Now referring to the figures, FIG. 4 shows a schematic representation of a catalytic process 100 for the production of oxidized reaction products from a lignin-containing material in accordance with one aspect of the presently disclosed and/or claimed inventive concept(s). More particularly, process 100 can be used to produce oxidized reaction products via a mechanocatalytic process using an oxidation catalyst. In one particular embodiment, the process 100 is used to catalyze the oxidative conversion of a lignin-containing material to one or more oxidized reaction products comprising at least one of vanillin, syringealdehyde, vanillic acid, and syringic acid using an oxidation catalyst in a mechanocatalytic reactor. The lignin-containing material and the oxidation catalyst catalytically react under the application of mechanical force to produce such oxidized reaction products. In general, the process 100 is, therefore, a non-aqueous and solvent-free mechanocatalytic process for the production of oxidized reaction products such as vanillin, syringealdehyde, vanillic acid, and syringic acid.

In step 102, a quantity of a lignin-containing material is contacted with a quantity of oxidation catalyst. To accomplish this, the materials may be introduced into any suitable vessel and, preferably, the vessel in which the step of agitating will take place in step 104, for example, by any suitable method, and simultaneously or sequentially one after the other. In all embodiments, the aggregation of the lignin-containing material and the oxidation catalyst results in a non-aqueous and solvent-free reactant mixture suitable for a non-aqueous and solvent-free oxidative catalytic process.

The lignin-containing material (and/or referred to herein as simply "lignin") may be any material or mixture of materials having a lignin content. Thus, in one embodiment, the lignin-containing material may be a purified source of lignin and, may in certain embodiments, comprise greater than 1, 5, 10, 20, 30, 40, 50, 60, 70, 80, 90, 95, or even 100 percent pure lignin separated away from any contaminants and/or other reactive and non-reactive materials. In another embodiment, the lignin-containing material is a natural lignin feedstock, typically referred to as a "biomass." Exemplary biomass materials include wood, paper, switchgrass, wheat straw, agricultural plants, trees, agricultural residues, herbaceous crops, starches, corn stover, saw dust, and high cellulose municipal and industrial solid wastes. The nature or origin of the lignin-containing material should not be considered to be constraining to the processes and methods disclosed herein, i.e., the lignin-containing material is source and composition independent and one of ordinary skill in the art, given the present disclosure, would appreciate that the origin and composition of the lignin-containing material could be tailored or blended in such a manner to provide any number of different oxidized reaction products using the oxidation catalyst and reaction conditions disclosed herein. In one embodiment, given for exemplary purposes and not by way of limitation, the lignin-containing material may be obtained from a lignocellulosic material having a cellulose, hemicellulose, and lignin content and according to any of the known processes for obtaining material therefrom. Indeed, the inventors have found to date that a wide variety of lignin-containing materials that have been tested are suitable and appropriate for the processes and methods disclosed herein.

As mentioned above, it is contemplated that in one embodiment, the biomass material is a lignocellulosic material having a cellulose, hemicellulose, and lignin content. Typically, in such a lignocellulosic material, the cellulose, hemicellulose, and lignin are bound together in a complex gel structure along with small quantities of extractives, pectin, protein, and ash. A substantial benefit of the presently disclosed and/or claimed inventive concept(s) is that when the lignin-containing material is a lignocellulosic material, the lignin does not have to be separated away from the cellulose and/or hemicellulose prior to catalytically reacting with the oxidation catalyst, thereby eliminating a significant portion of the waste component from the process and eliminating the need to purify the lignin-containing material before catalytically reacting the lignin-containing material with the oxidation catalyst. Any quantity of lignin-containing material may be provided and used in the presently disclosed and/or claimed inventive concept(s) and the particular ratios of reactants disclosed herein should be considered as non-limiting examples and/or non-limiting embodiments merely given for purpose of explanation.

The oxidation catalyst may be any solid material having an oxidative catalytic activity under the process and reaction conditions described herein. In one embodiment, such reaction conditions comprise a mechanocatalytic process. The oxidation catalyst functions in the same phase as the reactants and, pursuant to the presently disclosed and/or claimed inventive concept(s), the oxidation catalyst is in the solid phase as is the lignin-containing material. The reactants (i.e., the lignin-containing material and the oxidation catalyst) catalytically react with one another, therefore, in a non-aqueous and solvent-free environment.

The oxidation catalyst may be more particularly defined as a solid oxidation catalyst that releases oxygen into the reaction and takes it up from the atmosphere in which the catalytic reaction is taking place. In one specific but non-limiting embodiment, the oxidation catalyst comprises a metal oxide containing at least one of a transition metal element or lanthanide compound. The term "at least one of a transition metal element or lanthanide compound" means one or more of the chemical elements with atomic numbers 21 through 112, from scandium through copernicium. As used herein, the term "transition metal" or "transition element" or "transition metal element" means an element whose atom has an incomplete d sub-shell, or which can give rise to cations with an incomplete d sub-shell. The electronic structure of transition metal atoms is generally written as $[\ ]ns^2(n-1)d^m$, where the inner d orbital has more energy than the valence-shell s orbital. In divalent and trivalent ions of the transition metals, the situation is reversed such that the s electrons have higher energy.

Consequently, an ion such as $Fe^{2+}$ has no s electrons: it has the electronic configuration $[Ar]3d^6$ as compared with the configuration of the atom, $[Ar]4s^23d^6$.

As used herein, the term lanthanide compound means one or more of the fifteen chemical elements with atomic numbers 57 through 71 from lanthanum through lutetium. The informal chemical symbol Ln is used in general discussions of lanthanide chemistry to refer to any lanthanide. All but one of the lanthanides are f-block elements, corresponding to the filling of the 4f electron shell; lutetium, a d-block element, is also generally considered to be a lanthanide due to its chemical similarities with the other fourteen. All lanthanide elements form trivalent cations, $Ln^{3+}$, whose chemistry is largely determined by the ionic radius, which decreases steadily from lanthanum to lutetium. The electronic structure of the lanthanide elements, with minor exceptions is $[Xe]6s^24f^n$. In their compounds, the 6s electrons are lost and the ions have the configuration $[Xe]4f^m$. The chemistry of the lanthanides differs from main group elements and transition metals because of the nature of the 4f orbitals. These orbitals are "buried" inside the atom and are shielded from the atom's environment by the 4d and 5p electrons. As a consequence of this, the chemistry of the elements is largely determined by their size, which decreases gradually from 102 pm ($La^{3+}$) with increasing atomic number to 86 pm ($Lu^{3+}$), the so-called lanthanide contraction. All the lanthanide elements exhibit the oxidation state +3. In addition $Ce^{3+}$ can lose its single f electron to form $Ce^{4+}$ with the stable electronic configuration of xenon. Also, $Eu^{3+}$ can gain an electron to form $Eu^{2+}$ with the f7 configuration which has the extra stability of a half-filled shell. Promethium is effectively a man-made element as all its isotopes are radioactive with half-lives shorter than 20 years. In terms of reduction potentials, the $Ln^{0/3+}$ couples are nearly the same for all lanthanides, ranging from −1.99 (for Eu) to −2.35 V (for Pr). Thus, these metals are highly reducing, with reducing power similar to alkaline earth metals such as Mg (−2.36 V). According to the concept of hard and soft acids and bases (HSAB) established by Pearson, lanthanide +3 ions are considered to be hard acids, falling between Mg(II) and Ti(IV) in the established scale. Lanthanides therefore complex preferentially to hard bases such as oxygen donor ligands. The strong affinity of lanthanides for oxygen is further evidenced by the bond dissociation energies for the gas phase dissociation of diatomic lanthanide oxides (LnO). For example, although they are among the lowest values for lanthanides, both SmO (136 kcal/mol; 1 cal=4.18 J) and Yb (95 kcal/mol) exhibit values significantly higher than that for MgO (86 kcal/mol).

In one embodiment, the oxidation catalyst is a transition metal oxide or lanthanide metal oxide. Exemplary lanthanide oxides that may comprise the oxidation catalyst for use in the presently disclosed and/or claimed inventive concept(s) include Cerium oxide ($CeO_2$) although one of ordinary skill in the art will appreciate that any lanthanide metal oxide may be used in the process of the presently disclosed and/or claimed inventive concept(s). Exemplary transition metal oxides that may comprise the oxidation catalyst for use in the presently disclosed and/or claimed inventive concept(s) include Manganese oxide ($MnO_2$), such as K-Birnessite, although one of ordinary skill in the art will appreciate that any transition metal oxide may be used in the process of the presently disclosed and/or claimed inventive concept(s). Additionally and in an alternative embodiment, the oxidation catalyst may be a layered porphyrin-like solid such as hexagonal carbon nitride (h-$C_3N_4$) that has oxidative catalytic activity with respect to lignin in the processes and methods disclosed and/or claimed herein. Porphyrins are heterocyclic macrocycles composed of four modified pyrrole subunits interconnected at their a carbon atoms via methine bridges (=CH—). Porphyrins are aromatic—that is, they obey Hückel's rule for aromaticity, possessing 4n+2 π electrons (n=4 for the shortest cyclic path) delocalized over the macrocycle. The parent porphyrin is porphine, and substituted porphines are called porphyrins. Fully condensed hexagonal carbon nitride consists of sheets of melon units linked in a porous array resulting in openings very similar to porphyrin. Although not technically a "catalyst," it has also been found that metal oxides such as CuO and $Ag_2O$ can also depolymerize lignin, without the addition of a solvent or base, to the oxidized reaction products which, in at least one embodiment, comprise vanillin, syringealdehyde, vanillic acid, and syringic acid.

The oxidation catalyst may comprise up to 100 weight percent of a single transition metal oxide, lanthanide metal oxide, or layered porphyrin-like solid. In other embodiments, the oxidation catalyst may comprise at least two transition metal oxides, lanthanide metal oxides, and/or layered porphyrin-like solids in varying weight percent amounts. Additionally, the oxidation catalyst may comprise one or more non-catalytically active substrate or support materials. As such, it should be appreciated by one of ordinary skill in the art that it is preferable that the oxidation catalyst comprise a catalytic material containing a catalytically active amount of a transition metal oxide, lanthanide metal oxide, and/or layered porphyrin-like solid such as, but not by way of limitation, Cerium oxide, Manganese oxide, Copper oxide, Silver oxide, and/or hexagonal carbon nitride, for example.

Without wishing to be bound by any particular method of reaction, it is believed that the transition metal oxides, lanthanide metal oxides, or layered porphyrin-like solids are particularly useful as the oxidation catalyst for use in the presently disclosed and/or claimed inventive concept(s). In the presently disclosed and/or claimed inventive concept(s), it is believed that the agitating step 104 (as described herein) provides the kinetic energy and pressures necessary for catalysis to occur. As such, the oxidation catalyst is capable of converting lignin within the lignin-containing material to oxidized reaction products such as vanillin, syringealdehyde, vanillic acid, and syringic acid.

Although the lignin-containing material and/or the oxidation catalyst may have an inherent water content, it should be understood that the reactants, either alone or in combination, are still to be considered in a solid or non-aqueous phase. It should be understood, however, that the existence of such an amount of inherent water in the reactants should not be interpreted to mean that the reaction (i.e., the agitating step 104) occurs in an aqueous environment: rather, while some minor amount of water may be present, the mechanocatalytic reaction between the lignin-containing material and the oxidation catalyst is carried out in a non-aqueous (and solvent-free) environment and the lignin-containing material and the oxidation catalyst should be understood to be in a solid form. In one embodiment, when the lignin-containing material and the oxidation catalyst are contacted in step 102 and agitated in step 104, the free water content of the collective mixture of the reactants (i.e., the inherent water of the lignin-containing material and the oxidation catalyst) is less than about 45% by weight of the materials (thereby maintaining the reactants in a solid and/or non-aqueous environment) and, more preferably, the free water content of the collective mixture of the reactants is less than about 30% by weight, less than about 20% by weight, less than about 10% by weight, and from about less than about 5% by weight.

The ratio of the lignin-containing material to the oxidation catalyst is such that the depolymerization of the lignin and the formation of oxidized reaction products is optimized. Generally, the catalytic efficiency is optimized by determining a ratio of the lignin-containing material to the oxidation catalyst, wherein a surface interaction of the lignin-containing material and the oxidation catalyst is maximized and the production of specified or targeted oxidized reaction products is optimized. In one embodiment, but not by way of limitation, the lignin-containing material and the oxidation catalyst are provided in a ratio of from about 20:1 to about 1:1.

It is also contemplated that the process 100 is preferably performed at ambient temperature but may also occur at a temperature in a range of from about −5° C. to about 146° C. Although the term "ambient temperature" should be understood as the purposeful absence of external heating or cooling, it is also contemplated that the reactants and reaction mixture may autogenously provide additional heat through exothermic reactions and such a process is also considered for the purposes of this disclosure as occurring at "ambient temperature". Additionally, it is contemplated that the process 100 be performed without the addition of water or other solvent to the reactant mixture. Of course, although the process is disclosed and described as occurring in a non-aqueous and solvent-free environment, the water content of the reactant mixture may be up to about 40% by weight and yet still be considered as comprising a non-aqueous and solvent-free mixture. As such, it may be desirable in some situations to add some amount of water to the reactant mixture in order to maintain the amount of water within the reactant mixture to less than or about 40% by weight.

As would be readily apparent to one of ordinary skill, the ability to perform the process 100 according to the presently disclosed and/or claimed inventive concept(s) provides an efficient and effective means of producing oxidized reaction products, including at least vanillin, syringealdehyde, vanillic acid, and syringic acid, from a lignin-containing material using an oxidation catalyst in a non-aqueous and solvent-free environment on a large commercial batch or continuous manufacturing scale.

In step 104, the lignin-containing material and the oxidation catalyst are agitated for a time sufficient to provide a reaction product-containing solid, powdered, and/or liquid oxidized reaction products. The agitation may take place in any suitable vessel or reactor. In one embodiment, the agitating step 104 takes place in a ball, roller, jar, hammer, attrition, or shaker mill. The mills generally grind the reactants by placing them in a housing along with one or more grinding elements and imparting motion to the housing. The housing is typically cylindrical in shape and the grinding elements and/or milling media (as discussed herein) are typically steel balls, but may also be rods, cylinders, or other shapes. The containers and grinding elements can be made from the same material. Milling media may be for example, but not by way of limitation, 440C stainless steel balls ½ inch in diameter. As used herein, the term "milling" should be understood to be the agitating step 104 wherein the reactants (i.e., the lignin-containing material and the oxidation catalyst) are brought into contact with one another as well as with the milling media within the reactor. During the agitation step 104, the reactants catalytically react to form the oxidized reaction products. Once again, the reactants and the milling media are agitated in step 104 in a substantially non-aqueous environment and in a solid state.

As the container is rolled, swung, vibrated, or shaken, the inertia of the grinding elements and/or milling media causes the milling media to move independently into each other and against the container wall, grinding the lignin-containing material and the oxidation catalyst thereby bringing the reactants into reactive contact with one another. In one embodiment, the mill is a shaker mill using steel balls as the milling media and shaking to agitate the lignin-containing material and the oxidation catalyst. The mills for use in the presently disclosed and/or claimed inventive concept(s) may range from those having a sample capacity of a gram or less to large industrial mills with a throughput of tons per minute. Such mills are available from SPEX CertiPrep of Metuchen, N.J., for example, Paul O. Abbe, Bensenville, Ill., or Union Process Inc., Akron, Ohio. For some mills, such as a steel ball mill from Paul O. Abbe, the optimal fill volume is about 25% of the total volume of the mill. The number of steel balls (i.e., the milling media) required for the process 100 is typically dependent upon the amount of kinetic energy available. High energy milling like that in a shaker mill will require less milling media than lower energy milling methods such as rolling mills. For shaking mills, a ball to sample mass ratio (i.e., a milling media to reactant mass ratio) of about 12:1 is sufficient. For rolling mills, a ball to sample mass ratio (i.e., a milling media to reactant mass ratio) of about 30:1 at a rolling rate sufficient to maintain tumbling is acceptable for use. Lower mass ratios can be obtained by increasing the amount of kinetic energy available to the system. In a roller mill, this can be achieved through the optimization of mill geometry and the rotational velocity of the mill.

A significant advantage of the presently disclosed and/or claimed inventive concept(s) is that the processes described herein can be performed at ambient temperature without the need for added heat, cooling, or modifying pressure. Instead, the processes, including the agitation step 104, can be performed under ambient conditions. Without wishing to be bound by theory, it is believed the agitating step 104 of the lignin-containing material with the oxidation catalyst, such as in with the aforementioned mills, provides the process with the kinetic energy required for catalysis. Moreover, it is further believed that the agitating step 104 also allows more of the lignin-containing material to come into contact with catalytic sites on the oxidation catalyst. Even further, it is believed that the heat created by the agitating step 104 facilitates the depolymerization of the lignin by increasing the rate of oxidative cleavage. In one embodiment, the agitating step 104 may occur at a controlled temperature of between about −5 to about 146 degrees C. It is contemplated that the agitating step 104 may occur at any temperature degree value within this range (rounded to the nearest 0.5 centigrade unit), or within any sub-ranges within this range (rounded to the nearest 0.5 centigrade unit).

After the step of agitating 104, the oxidized reaction products may be separated from any unreacted lignin-containing material and/or oxidation catalyst (as well as any other contaminants and/or other unreactive components) in step 105. Typically, the oxidized reaction products obtained after the step of agitating 104 comprises at least one of vanillin, syringealdehyde, vanillic acid, syringic acid, and combinations thereof. The oxidized reaction products may be in a solid, semi-solid, or liquid state although in a preferred but non-limiting embodiment it is contemplated that the reaction products will be substantially in a solid state.

When using a mill as described herein, the mechanocatalytic processes described are generally carried out as a batch process. In addition, the vessel where the agitating and oxidation reaction takes place may be performed in a continuous attritter, which is commercially available from Union Process, Akron, Ohio. This device more generally allows the process to be carried out as a continuous process.

The milling time performed in the agitating step 104 may have an effect on the extent of catalytic conversion of the lignin-containing material into the oxidized reaction products. It is contemplated that from at least about 100% to about 5% of the lignin-containing material will be catalyzed to form the oxidized reaction product in various embodiments of the presently disclosed and/or claimed inventive concept(s). It is appreciated that higher or lower efficiencies of the catalytic conversion of the lignin-containing material to the oxidized reaction products may be obtained by selecting from the various oxidation catalysts (discussed hereinabove), milling time, and by modifying the ratio of the lignin-containing material to the oxidation catalyst.

Referring again to FIG. 1, after step 104 of agitating, the oxidized reaction products may be separated via the separating step 105 in order to provide individual compounds (i.e., the oxidized reaction products) which may be quantitated and/or used in the preparation of other chemicals of interest. Any suitable method of determining the amount of oxidation reaction product may be used, such as by chromatographic methods well known in the art. Moreover, the presence of particular oxidized reaction products may be confirmed by any suitable chromatography method, such as thin-layer chromatograph, gas chromatography (GC), high-pressure liquid chromatography (HPLC), GC-MS, LC-MS, or any other suitable method known in the art. The oxidized reaction products may be separated out individually and stored. Alternatively, at least a portion of the oxidized reaction products may be sent to a subsequent processing step prior to separating out individual oxidized reaction products from one another. In either event, one or more of the oxidized reaction products (either individually or in a mixture) may be sent to a secondary process to convert the oxidized reaction products into secondary products. For example, but not by way of limitation, such secondary products may comprise seal swelling agents, biofuel additives, food and neutraceutical additives, flavoring agents, specialty chemical precursors, antibacterial agents, and other types of pharmaceutical and medicinal compounds.

Since the oxidation catalyst is acting as a catalyst (and not as a chemical reactant) in the oxidative catalytic conversion of the lignin-containing material, the oxidation catalyst may be recycled in whole or in part. Thus, optionally, the oxidation catalyst (as a separated product and/or in combination with the oxidized reaction products leaving step 104) may be directed to recycling step 122 to prepare the oxidation catalyst for reuse in subsequent contacting step(s) 102 and/or agitating step(s) 104. If no preparation step is necessary for the recycling of the oxidation catalyst, the oxidation catalyst material can be immediately reused in contacting step 102. In either instance, the oxidation catalyst is optionally recycled and reused to catalyze further lignin-containing materials to oxidized reaction products by starting the process again at step 102 and/or step 104. Additional oxidation catalyst may be added as needed to supplement the recycled oxidation catalyst when repeating steps 102 and/or 104. Accordingly, a significant advantage of the presently disclosed and/or claimed inventive concept(s) is that at least a portion of the oxidation catalyst may be reused continuously, thereby saving considerable material and expense.

Examples

As shown below in Table 1, oxidative catalytic reactions of the lignin-containing material with differing oxidation catalysts were performed in, and agitation was supplied by, SPEX 8000M (single) and SPEX 8000D (dual) mixer mills (SPEX CertiPrep, Metuchen, N.J.). Enough oxidation catalyst and lignin-containing material (i.e., douglas fir wood shavings) were weighed to produce a total mass of 1 gram. The proportions were varied to meet the ratios specified in Table 1. If no ratio is specified, the ratio was 1:1. The oxidation catalyst/lignin-containing material was placed in a flat bottom SPEX milling vial approximately 65 mL in volume. Three ½ inch ball bearings were used as the milling media. Once again, milling was performed in 8000M (single) and 8000D (dual) mixer/mills. Milling vials, lid, and ball bearings were all constructed from 440C stainless steel. All samples were milled for two hours.

A small amount of the oxidized reaction products (along with any unreacted materials intermixed with the oxidized reaction products) was placed in a 1.5 mL plastic centrifuge tube. 1.24 mL of HPLC solvent (an 80:20 mixture of 0.1% trifluoroacetic acid in water:acetonitrile) was added. The tube was sonicated and centrifuged. The supernatant was decanted, filtered, and placed in an autosampler vial for HPLC analysis which was conducted using a UV detection wavelength of 280 nm and an appropriate solvent gradient.

Table 1 indicates peak ratios for organosolv lignin catalytically processed with Manganese, Cerium, and hexagonal carbon nitride (h-$C_3N_4$) oxidation catalysts. The oxidative reagent CuO and pure lignin are included in Table 1 for purpose of comparison. The values in Table 1 are normalized to the intensity of the syringealdehyde peak. K-Birnessite is a layered manganese dioxide ($MnO_2$) with a formula close to $K_{0.31}MnO_2$.

TABLE 1

| | Vanillic Acid | Syringic Acid | Vanillin | Syringic Acid/ Syringaldehyde | Vanillic Acid/ Vanillin |
|---|---|---|---|---|---|
| Pure Lignin | 0.22 | 0.75 | 0.90 | 0.75 | 0.24 |
| 25% CuO | 0.46↑ | 1.44↑ | 0.87↓ | 1.44 | 0.52 |
| 50% K-Birnessite | 0.17↓ | 0.29↓ | 0.87↓ | 0.29 | 0.19 |
| 5% K-Birnessite | 0.79↑ | 2.11↑ | 1.59↑ | 2.11 | 0.50 |
| 50% K-Birnessite/$CeO_2$ (3:1) | 0.26↑ | 0.31↑ | 0.92↑ | 0.31 | 0.28 |
| 50% Mn/Ce Cluster (6:1) | 1.90↑ | 0.57↓ | 0.68↓ | 0.57 | 2.80 |
| 50% $CeO_2$ | 0.26↑ | 0.90↑ | 0.90 | 0.90 | 0.29 |
| 50% h-$C_3N_4$ | 0.11↓ | 0.50↓ | 0.90 | 0.50 | 0.12 |

As can be observed from Table 1, the inclusion of an oxidation catalyst comprising a 5% K-Birnessite and a 50% mixture of K-Birnessite and $CeO_2$ (3:1) in the mechanocatalytic process provided a significant increase in the amount of vanillin in the oxidized reaction products as compared to pure lignin. The arrows in Table 1 indicate an increase or decrease in the peak ratios as compared to pure lignin.

The presently disclosed and/or claimed inventive concept(s), in various embodiments, includes components, methods, processes, systems and/or apparatus substantially as depicted and described herein, including various embodiments, subcombinations, and subsets thereof. Those of skill in the art will understand how to make and use the presently disclosed and/or claimed inventive concept(s) after understanding the present disclosure. The presently disclosed and/or claimed inventive concept(s), in various embodiments, includes providing devices and processes in the absence of items not depicted and/or described herein or in various embodiments hereof, including in the absence of such items as may have been used in previous devices or processes, e.g., for improving performance, achieving ease and/or reducing cost of implementation.

The foregoing discussion of the presently disclosed and/or claimed inventive concept(s) has been presented for purposes of illustration and description. The foregoing is not intended to limit the presently disclosed and/or claimed inventive concept(s) to the form or forms disclosed herein. In the foregoing Detailed Description for example, various features of the presently disclosed and/or claimed inventive concept(s) are grouped together in one or more embodiments for the purpose of streamlining the disclosure. This method of disclosure is not to be interpreted as reflecting an intention that the claimed presently disclosed and/or claimed inventive concept(s) requires more features than are expressly recited in each claim. Rather, as the following claims reflect, presently disclosed and/or claimed inventive concept(s) lie in less than all features of a single foregoing disclosed embodiment. Thus, the following claims are hereby incorporated into this Detailed Description, with each claim standing on its own as a separate preferred embodiment of the presently disclosed and/or claimed inventive concept(s).

Moreover, though the description of the presently disclosed and/or claimed inventive concept(s) has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. A method for the production of an oxidized reaction product comprising at least one of vanillin, syringaldehyde, vanillic acid, and syringic acid, comprising the step of mechanocatalytically reacting an amount of a lignin containing material and an oxidation catalyst containing at least one of a 5% K-Birnessite, or a 50% mixture of K-Birnessite and $CeO_2$ in ratio of 3:1, in a non-aqueous and solvent-free environment for a period of time sufficient to produce the oxidized reaction product.

2. The method of claim 1, wherein the oxidation catalyst comprises a solid metal oxide comprising at least one of manganese oxides, cerium oxides, copper oxides, silver oxides, and combinations thereof.

3. The method of claim 2, wherein the oxidation catalyst comprises a solid metal oxide comprising at least one of manganese oxides, cerium oxides, and combinations thereof.

4. The method of claim 2, wherein the oxidation catalyst comprises hexagonal carbon nitride.

\* \* \* \* \*